United States Patent
Nichols et al.

(10) Patent No.: US 10,583,554 B2
(45) Date of Patent: Mar. 10, 2020

(54) INSTRUMENT TURNTABLE AND METHOD FOR USE

(75) Inventors: Michael J. Nichols, Brookline, MA (US); Louis J. Guarracina, Newburyport, MA (US)

(73) Assignee: HIGHRES BIOSOLUTIONS, INC., Woburn, MA (US)

( * ) Notice: Subject to any disclaimer, the term of this patent is extended or adjusted under 35 U.S.C. 154(b) by 723 days.

(21) Appl. No.: 13/141,766

(22) PCT Filed: Jan. 21, 2010

(86) PCT No.: PCT/US2010/021623
§ 371 (c)(1),
(2), (4) Date: Jun. 23, 2011

(87) PCT Pub. No.: WO2010/085546
PCT Pub. Date: Jul. 29, 2010

(65) Prior Publication Data
US 2011/0270445 A1    Nov. 3, 2011

Related U.S. Application Data

(60) Provisional application No. 61/146,061, filed on Jan. 21, 2009.

(51) Int. Cl.
*B25J 9/00* (2006.01)
*G01N 35/00* (2006.01)

(52) U.S. Cl.
CPC ........ *B25J 9/0096* (2013.01); *G01N 35/0099* (2013.01); *G05B 2219/39105* (2013.01)

(58) Field of Classification Search
CPC . B25J 9/041; B25J 21/00; G05B 2219/39105; G01N 35/025; G01N 2035/00504; G01N 2035/0439; B01L 2200/025

USPC .......... 700/245, 248, 250, 255, 258; 422/64, 422/624, 209, 258, 259, 269–271; 436/45, 48

See application file for complete search history.

(56) References Cited

U.S. PATENT DOCUMENTS

| | | | |
|---|---|---|---|
| 5,320,808 A * | 6/1994 | Holen et al. | 422/64 |
| 5,537,741 A | 7/1996 | Peterson et al. | |
| 5,827,478 A * | 10/1998 | Carey et al. | 422/64 |
| 2001/0053336 A1 | 12/2001 | Hammer et al. | |
| 2002/0064867 A1 | 5/2002 | Clark et al. | |
| 2002/0164807 A1 | 11/2002 | Itaya et al. | |
| 2007/0237675 A1 | 10/2007 | Nichols et al. | |

FOREIGN PATENT DOCUMENTS

| | | | | |
|---|---|---|---|---|
| WO | WO 87/01336 | * | 3/1987 | B41J 11/58 |

OTHER PUBLICATIONS

Giffo-Schmitt, International Application No. PCT/US2010/021623, International Preliminary Report on Patentability, dated Aug. 4, 2011, 6 pages.

PCT International Search Report and Written Opinion; dated Mar. 9, 2010; 7 pages.

* cited by examiner

*Primary Examiner* — Spencer D Patton
(74) *Attorney, Agent, or Firm* — Perman & Green, LLP

(57) ABSTRACT

An instrument turntable is presented which allows an instrument to be installed into an automated system, yet that will still allow an operator to use the instrument manually, even while the automated system is running, without ever removing the instrument from the automated system.

17 Claims, 9 Drawing Sheets

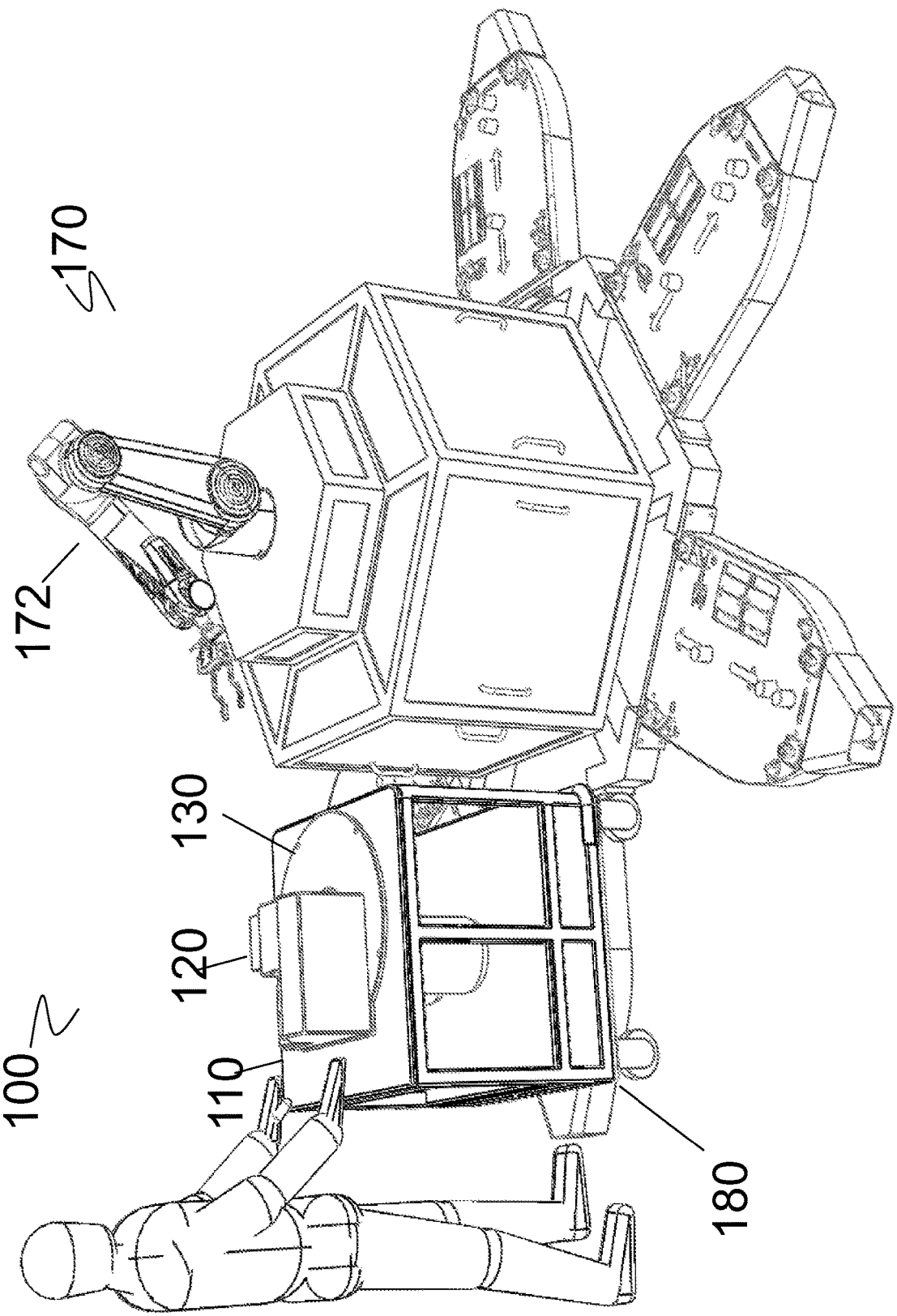

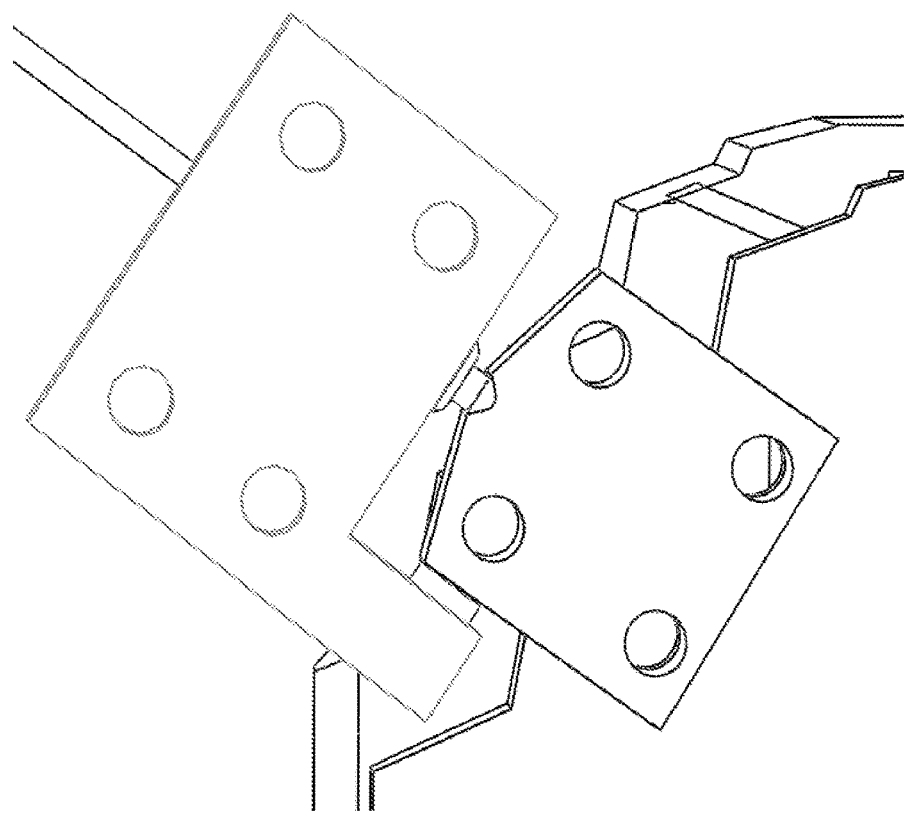
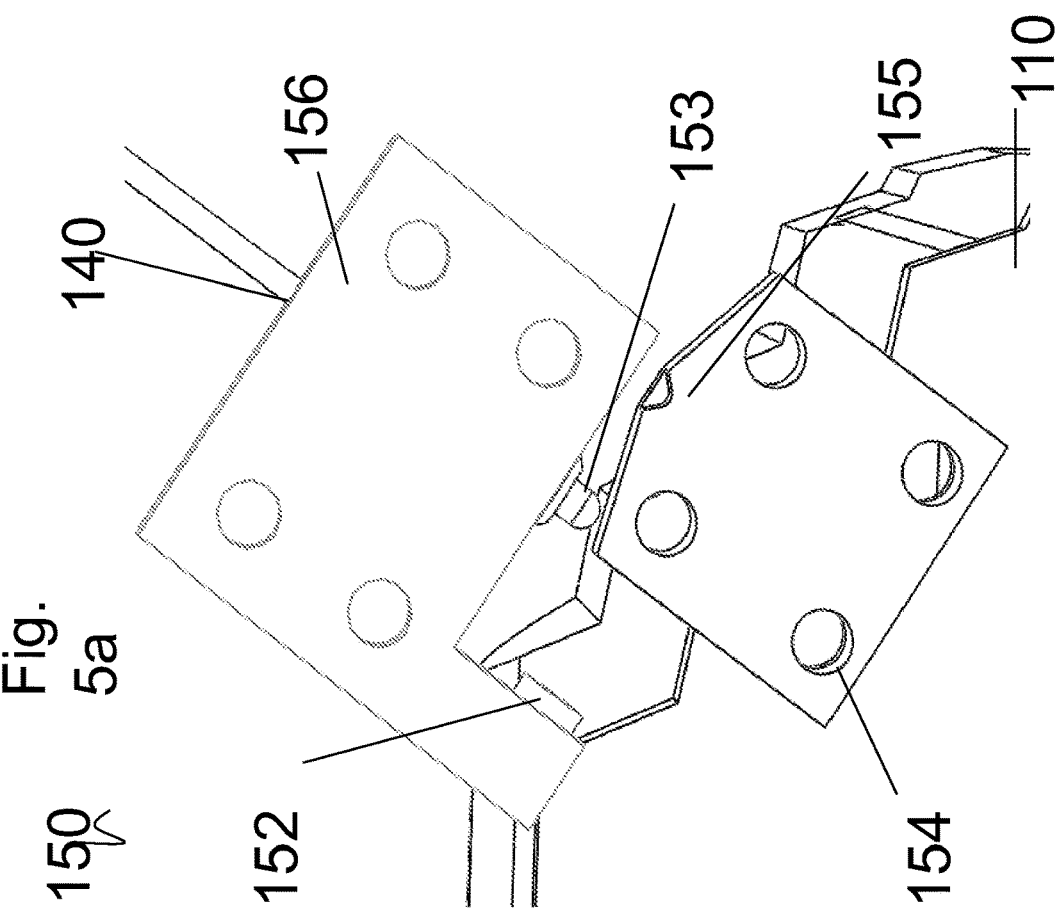

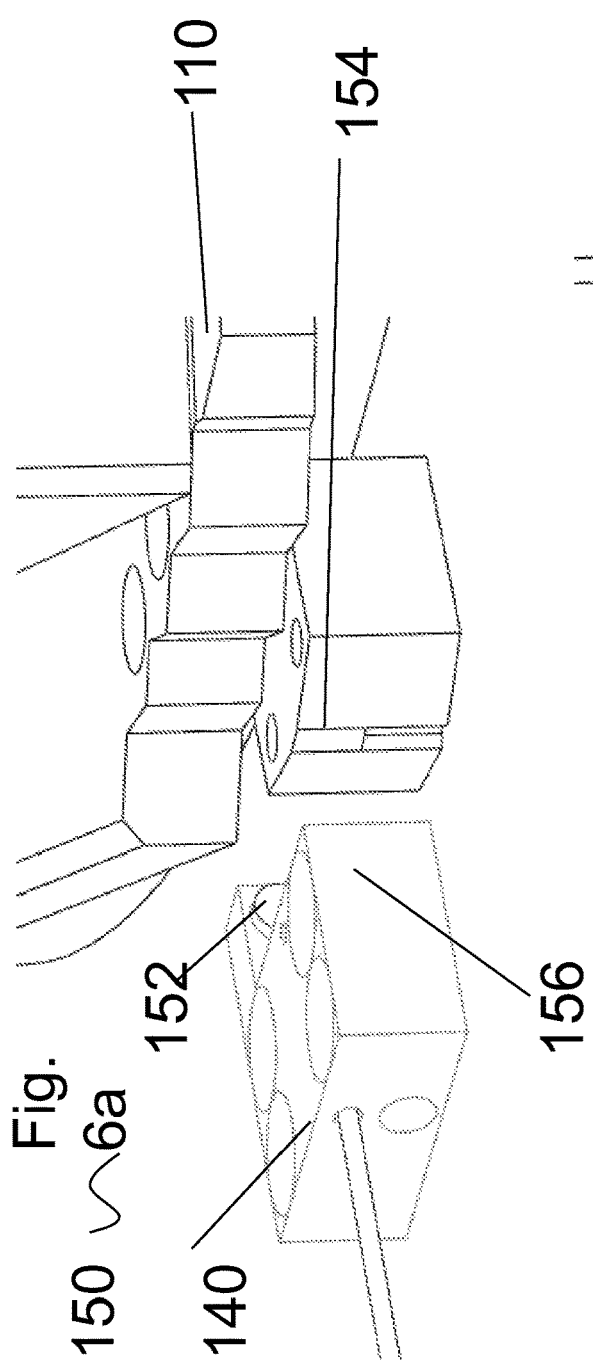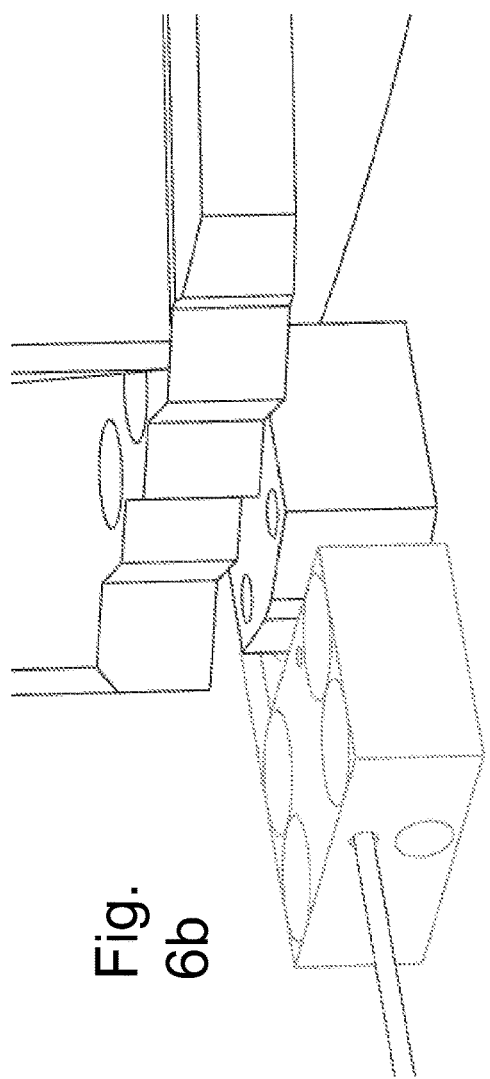

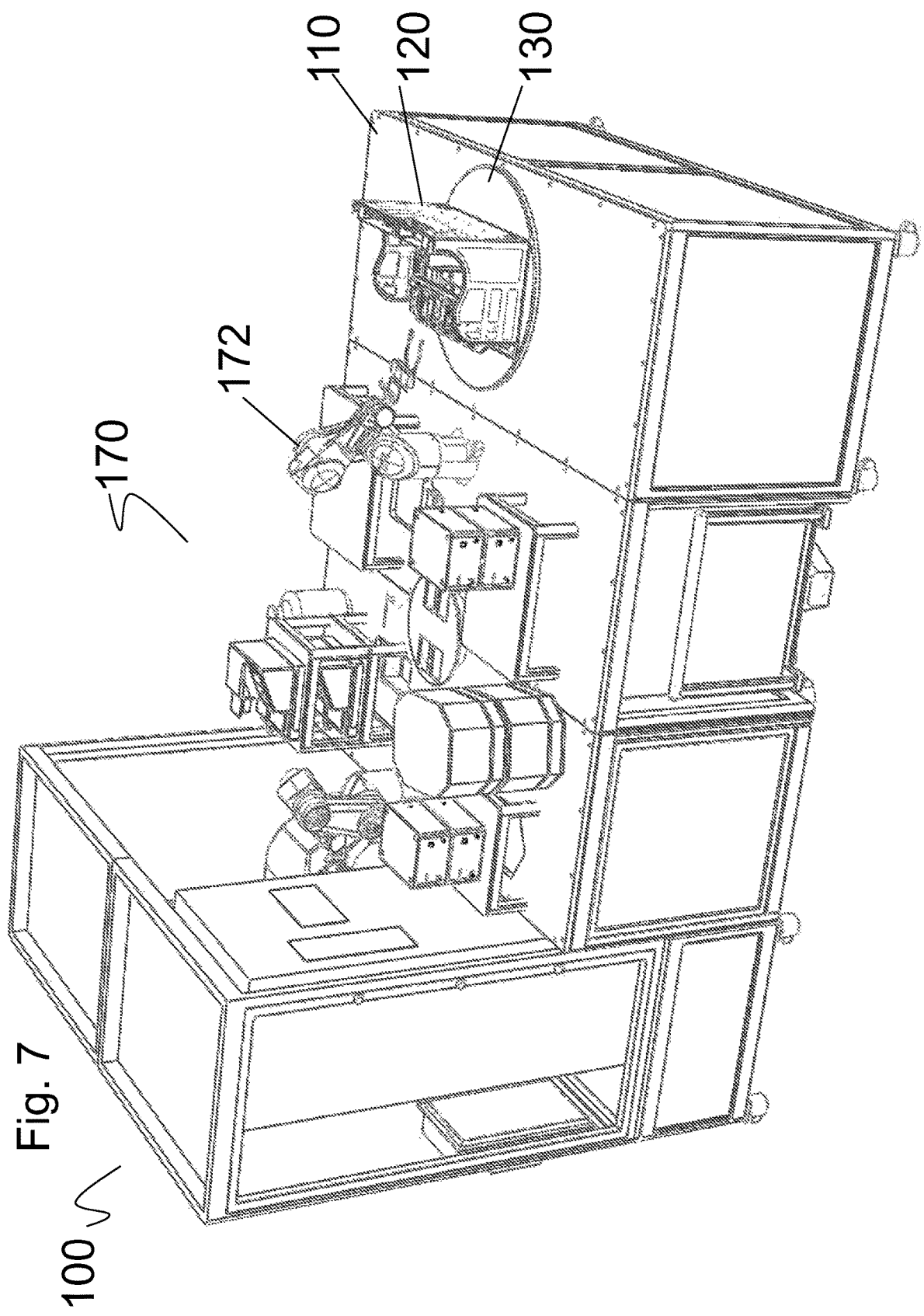

INSTRUMENT TURNTABLE AND METHOD FOR USE

CROSS REFERENCE TO RELATED APPLICATIONS

This application is a National Stage of International Application No. PCT/US2010/021623, having an International Filing Date of 21 Jan. 2010, which designated the United States of America, and which International Application was published under PCT Article 21(2) as WO Publication No. 2010/085546 A1, which claims priority from and the benefit of U.S. Provisional Patent Application No. 61/146,061, filed on Jan. 21, 2009, the disclosures of which are incorporated herein by reference in their entireties.

TECHNICAL FIELD

This invention relates to an instrument turntable which allows an instrument to be installed into an automated system and to still be used manually.

BACKGROUND OF THE INVENTION

Most laboratory instruments that are integrated in automated robotic systems have a distinct front side that comprises most of the user interface. The front of an instrument can contain buttons, switches, knobs, indicator lights, and screens, all of which must be touched or seen by an operator in order to use the instrument. Generally, materials must be presented to or removed from the instrument in the course of operation (e.g., microtiter plates) at the front of the instrument.

When such an instrument is integrated into an automated robotic system, it must be positioned in the system such that the front of the instrument is facing toward the robot, so that the robot can pick up and place materials (e.g., microtiter plates) on the instrument. However, in this orientation, the back of the instrument is presented to an operator who approaches the instrument from outside the system (for safety reasons, it is rarely possible for an operator to routinely approach an instrument from "inside" the system, i.e., from the robot side). This makes it very difficult for an operator to use an integrated instrument.

Current methods of coping with this problem are undesirable. Some users remove the instrument from the automated system altogether when the instrument is needed for manual use, and must replace the instrument into its position in the automated system when it is needed for automated use. This is time-consuming, and may require re-teaching the robot, as the instrument may not be returned to precisely the same position when moved back into the automated system. Furthermore, for safety and other reasons it is generally not possible for instruments to be installed in or removed from an automated system while the system is in use, greatly limiting the flexibility of when the instrument may be moved on or off the system.

Other users may purchase two identical instruments; one for permanent installation in the automated system and the second for manual use, even if having two identical instruments means the user is wasting money on excess capacity.

SUMMARY OF THE INVENTION

A first aspect of the invention includes a system comprising: a surface for holding an instrument; a rotating element coupled to the surface to allow the surface to rotate; a sensor to detect a position of the surface; a member that locks the surface in a holding position; and means for sending a signal indicating the position of the surface from the sensor to an automated system including a robotic arm for accessing the instrument.

A second aspect of the invention includes a method comprising: providing a system comprising a surface for holding an instrument, a rotating element coupled to the surface to allow the surface to rotate, a sensor to detect a position of the surface, a member that locks the surface in a holding position, and means for sending a signal indicating the position of the surface from the sensor to an automated system including a robotic arm for accessing the instrument; placing the system in conjunction with the automated system including a robotic arm; and connecting the signal from the sensor to the automated system.

The advantages of this instrument turntable will be described with more detail below.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 3 shows a perspective view of an instrument on a turntable in conjunction with an automated system turned toward a user.

FIG. 5a shows a bottom perspective view of a locking mechanism according to some embodiments approaching a locked position and FIG. 5b shows a bottom perspective view of a locking mechanism according to some embodiments of the invention.

FIG. 6a shows a side perspective view of a locking mechanism according to some embodiments approaching a locked position and FIG. 6b shows a side perspective view of a locking mechanism according to some embodiments of the invention.

FIG. 7 shows a side perspective view of an instrument on a turntable in conjunction with an automated system.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
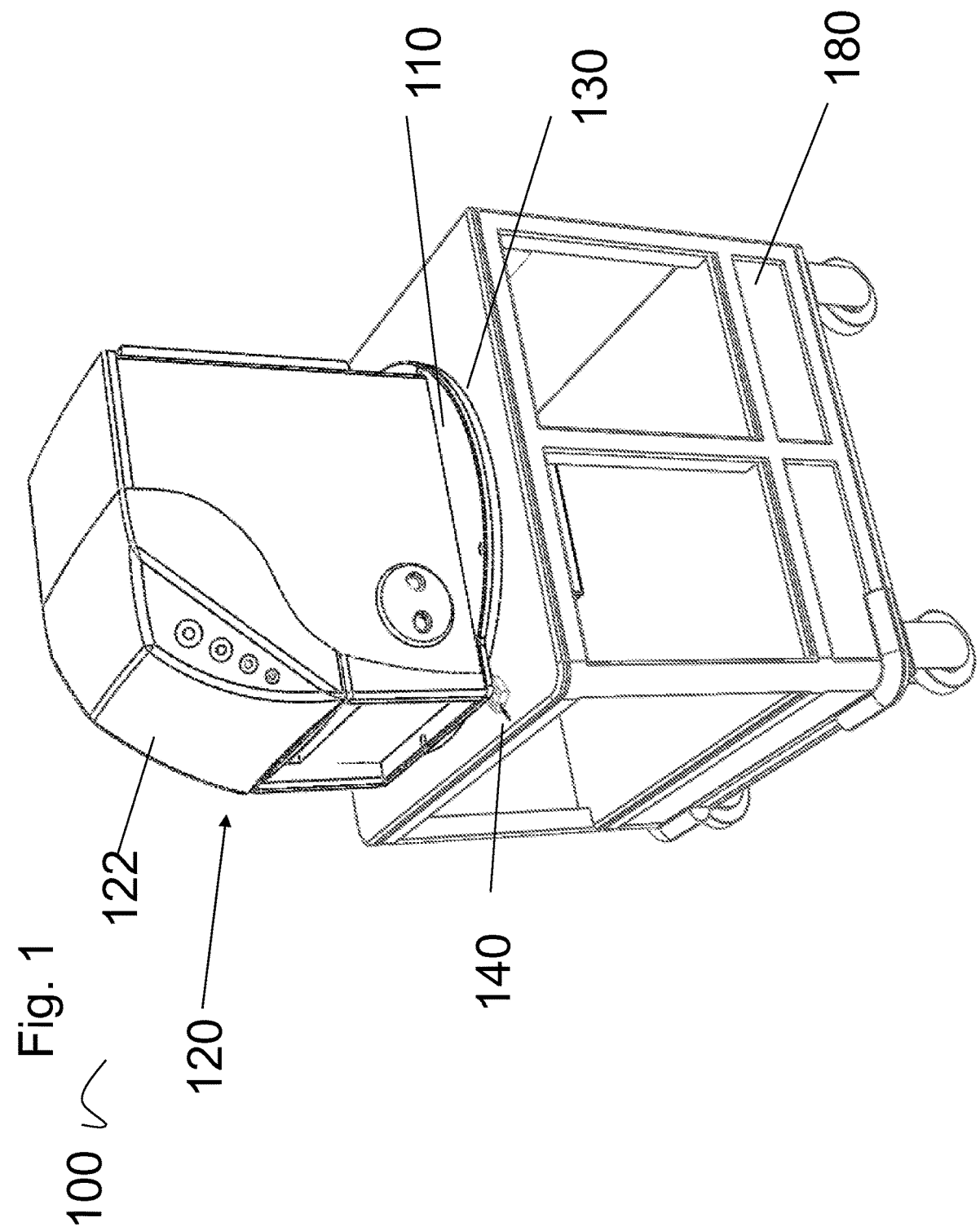
FIG. 1 shows a side perspective view of an instrument on a turntable according to an embodiment of the present invention.

A system 100 is presented, as seen in FIG. 1, comprising in one embodiment a surface 110 for holding an instrument 120. It is understood that surface 110 may be any surface used to contain an instrument 120, such as for example a countertop or a piece of nearly any material.

It can be appreciated that instrument 120 in one embodiment is a laboratory instrument which comprises a distinct front side that includes most of the user interface. The front 122 of such an instrument 120 may contain buttons, switches, knobs, indicator lights, and screens, all of which commonly may be touched or seen by an operator in order to use the instrument. Generally, materials may be presented to or removed from instrument 120 in the course of operation, such as microtiter plates, at the front of the instrument. It should be understood that instrument 120 may also include any laboratory instrument now known or later developed.

In one embodiment, system 100 may also include a rotating element 130 coupled to surface 110 to allow surface 110 to rotate. It should be noted that rotating element 130 may comprise a rotary turntable, as is known in the art. However, rotating element 130 may also comprise a set of linear rails, a set of curved rails, a hinge, a set of eccentric rotary bearings, or a set of non-parallel linear rails. In some embodiments, rotation of surface 110 may occur by more complex movements, such as a translation of surface 110.

System 100 may also comprise a sensor 140 to detect a position of surface 110. In one embodiment sensor 140 may include a proximity sensor which is capable of determining the position of surface 110. In another embodiment, sensor 140 may comprise an infrared beam sensor, a laser beam sensor, a rotary encoder, a linear encoder, or a linear differential transformer. Many compact sensors are known in the art which would be considered within the scope of the invention.

In one embodiment system 100 also may include a member 150 that locks surface 110 in a holding position. As seen in FIGS. 5a and 5b, member 150 may be a spring loaded ball catch. In this case, as can be appreciated, member 150 consists of two separate parts. The first part 154 is attached to surface 110 and has a receiver 155 for receiving spring loaded catch ball 153. The second part 156 is an assembly housing spring loaded catch ball 153 which is attached to a fixed part of system 100, which may also house sensor 140 as well. As surface 110 reaches a specified position, catch ball 153 pushes in allowing surface 110 to move into position, and pushes back out into receiver 155 to lock surface 110 in place. In another embodiment member may be one of a latch, a clamp, or a magnet. An alternative locking member 150 is depicted in FIGS. 6a and 6b. A number of locking members 150 are known in the art, the substitution of which would not be considered outside of the scope of the invention.

Figure 4B:
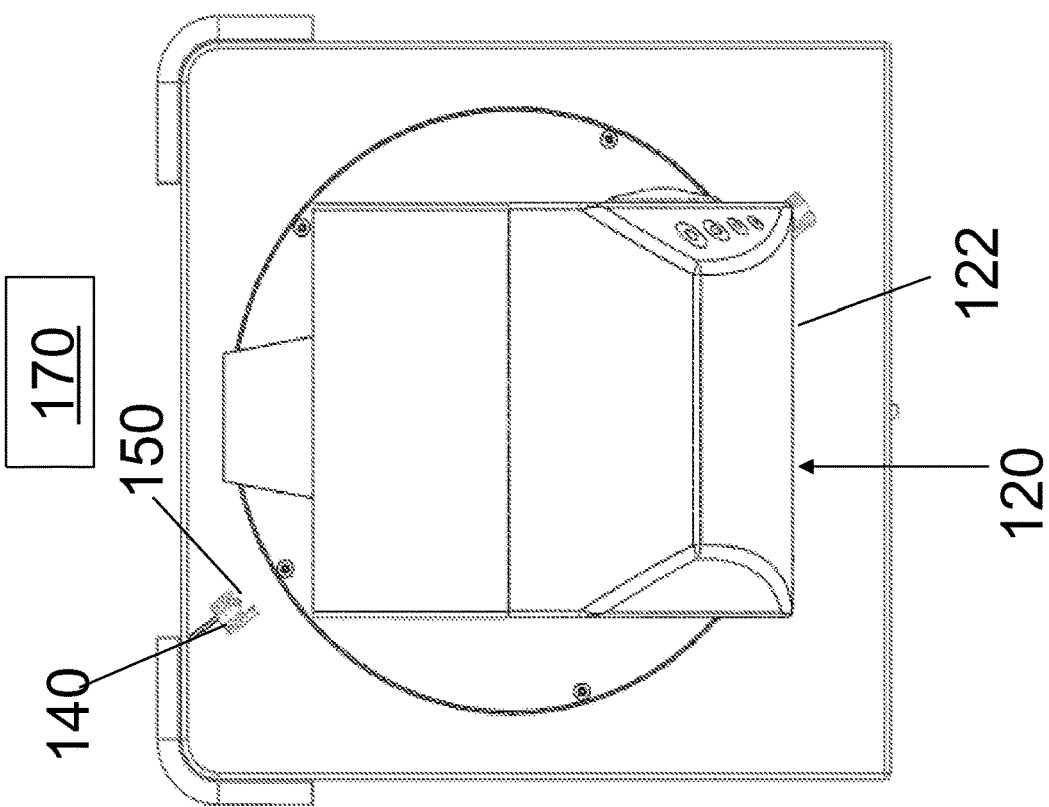
FIG. 4a shows a top perspective view of an instrument on a turntable rotated toward the automated system side and FIG. 4b shows a top perspective view of an instrument on a turntable rotated toward the manual access side.
Figure 4A:
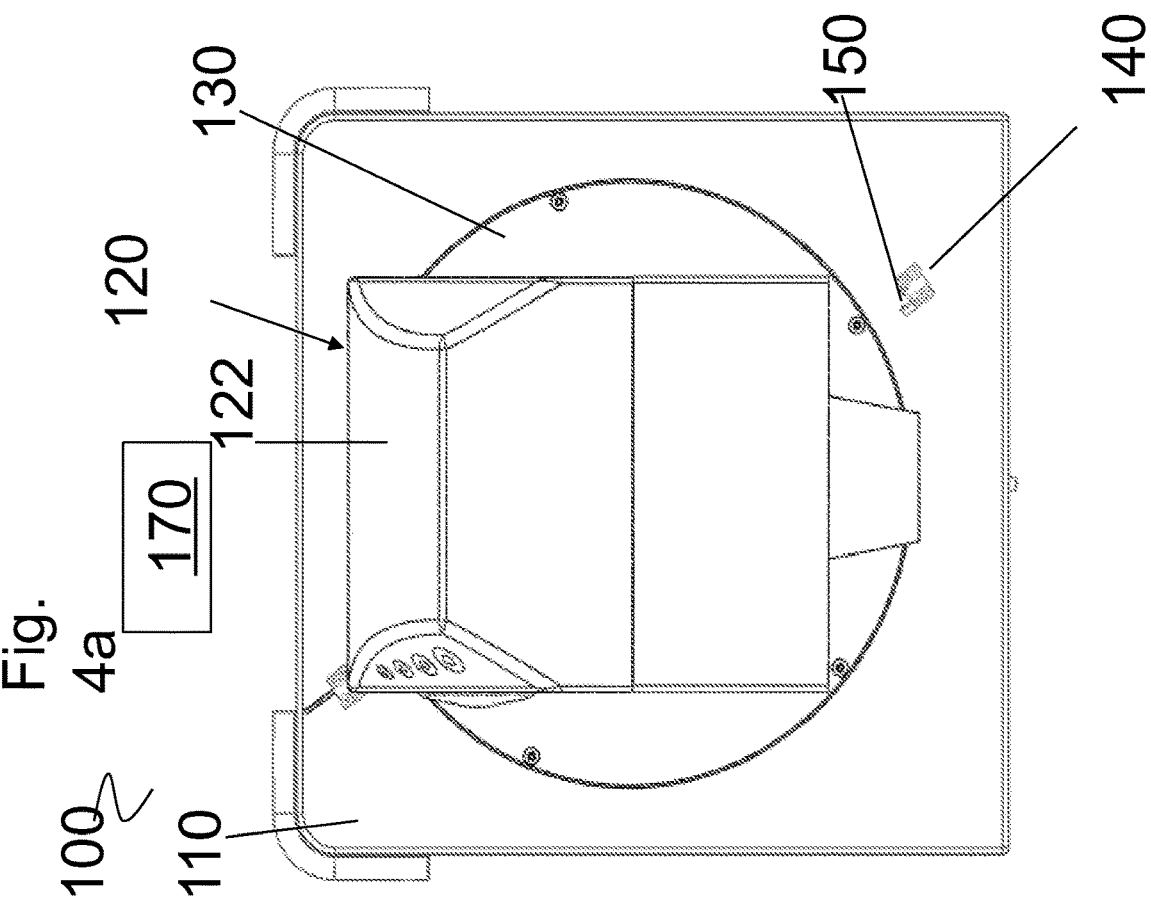

In some embodiments, member 150 locks surface 110 in a first position or a second position, as depicted in FIGS. 4a and 4b, wherein the first position is such that front 122 of instrument 120 faces an automated system 170, and the second position is such that instrument 120 faces away from automated system 170. It should be noted that two positions is a minimum embodiment. As is understood, instrument 120 may have side panels or multiple access points. In such a case, member 150 may lock surface 110 in many positions, facilitating convenient access to more than one position of surface 110 by a user. For example, if an error occurs in instrument 120, a user may need to access a removable side panel to determine the source of said error.

In one embodiment system 100 may also comprise a shock absorber 152 coupled to member 150 that locks surface 110, as shown in FIGS. 5a and 5b as well as FIGS. 6a and 6b. Shock absorber 152 serves to minimize jolting of instrument 120 when surface 110 is rotated into a position. In some embodiments shock absorber 152 may be a rubber or a foam pad. In this case, when member 150 is spring loaded catch ball 153, shock absorber 152 may be attached to spring loaded catch ball assembly 156 of member 150 at the stopping point. In another embodiment shock absorber 152 may comprise a pneumatic damper, a hydraulic damper, or a spring shock.

System 100 may further comprise an actuator (not shown) for turning surface 110. An actuator in some embodiments may include an electric actuator or a pneumatic actuator. In a further embodiment, actuator may also hold surface 110 in a position. In this case, member 150 may not be included as part of system 100, as an actuator can hold surface 110 in position and automatically move surface 110, also minimizing user exposure to areas near automated system 170.

Figure 2:
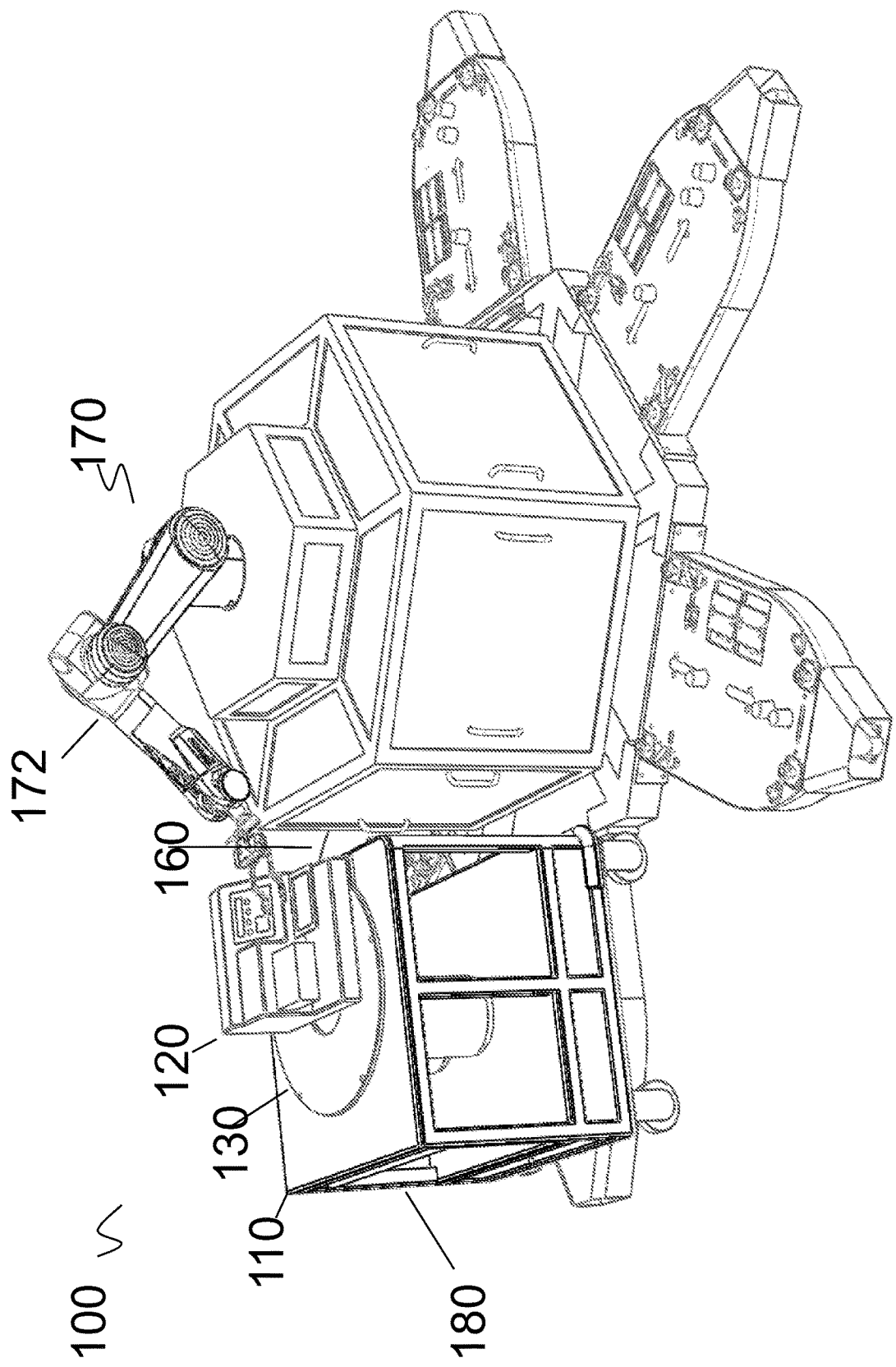
FIG. 2 shows a perspective view of an instrument on a turntable in conjunction with an automated system.

As shown in FIGS. 2 and 3, system 100 may include a mobile cart 180 for holding the surface 110. Mobile cart 180 allows instrument 120 on surface 110 to be installed in different automated systems 170 at the will of a user.

Still referring to FIG. 2, system 100 may also include a device or tool for sending a signal indicating the position of surface from sensor 140 to automated system 170 including a robotic arm 172 for accessing instrument 120. In one embodiment, wherein surface 110 is on a fixed surface, sensor 140 (FIG. 1) may be wired directly to an i/o module in a robot controller in automated system 170. As shown in FIG. 2, the device for sending signal is a wire 160 behind mobile cart 180. However, it should be understood that any device or tool for sending a signal could be utilized, including a wireless device. In the case that surface 110 is mounted on mobile cart 180, sensor 140 may send a signal to a digital i/o-to-Ethernet converter module which may be located on mobile cart 180. In such a case, the Ethernet signal may be routed through connectors on mobile cart 180 to automated system 170. The signal may continue through to an Ethernet router and into the control PC of automated system 170. In either case, one of the control units running the system (either the robot controller or the main system PC) is running software that directs and coordinates all motions of the robot.

Another embodiment of the invention includes a method comprising providing system 100 including surface 110 for holding instrument 120, rotating element 130 coupled to surface 110 to allow surface 110 to rotate, sensor 140 to detect a position of surface 110, member 150 that locks the surface 110 in a holding position, and a device 160 for sending a signal indicating the position of surface 110 from sensor 140 to automated system 170 including robotic arm 172 for accessing instrument 120. The method may further comprise placing system 100 in conjunction with automated system 170 including robotic arm 172. In a further embodiment, the method includes sending the signal from sensor 140 to automated system 170.

In one embodiment of the invention, in response to sensor 140 detecting that system 100 is facing automated system 170, the method includes allowing robotic arm 172 access to instrument 120 on system 100. In a further embodiment, in response to sensor 140 detecting that system 100 is not facing automated system 170, the method includes prohibiting robotic arm 172 from accessing instrument 120 on system 100. In this case, a control software package attached to automated system 170 receives an input signal from sensor 140 of system 100 indicating the position of surface 110. Before the control software directs robotic arm 172 to pick or place materials to or from instrument 120, it first determines whether sensor 140 of system 100 associated with instrument 120 indicates that surface 110 is in the robot access position, i.e. towards automated system 170. When such is the case, robotic arm 172 of automated system 170 accesses instrument 120 for the current procedure requiring access to instrument 120. When the case is such that sensor 140 determines that surface 110 is not in the robot access position, i.e. facing away from automated system 170, then robotic arm 172 does not access instrument 120. When such is the case, automated system 170 may instead perform other operations which do not involve that particular instrument 120. It should be noted that the same automated system 170, as such, may be placed in conjunction with more than one system as described herein.

Figure 8:
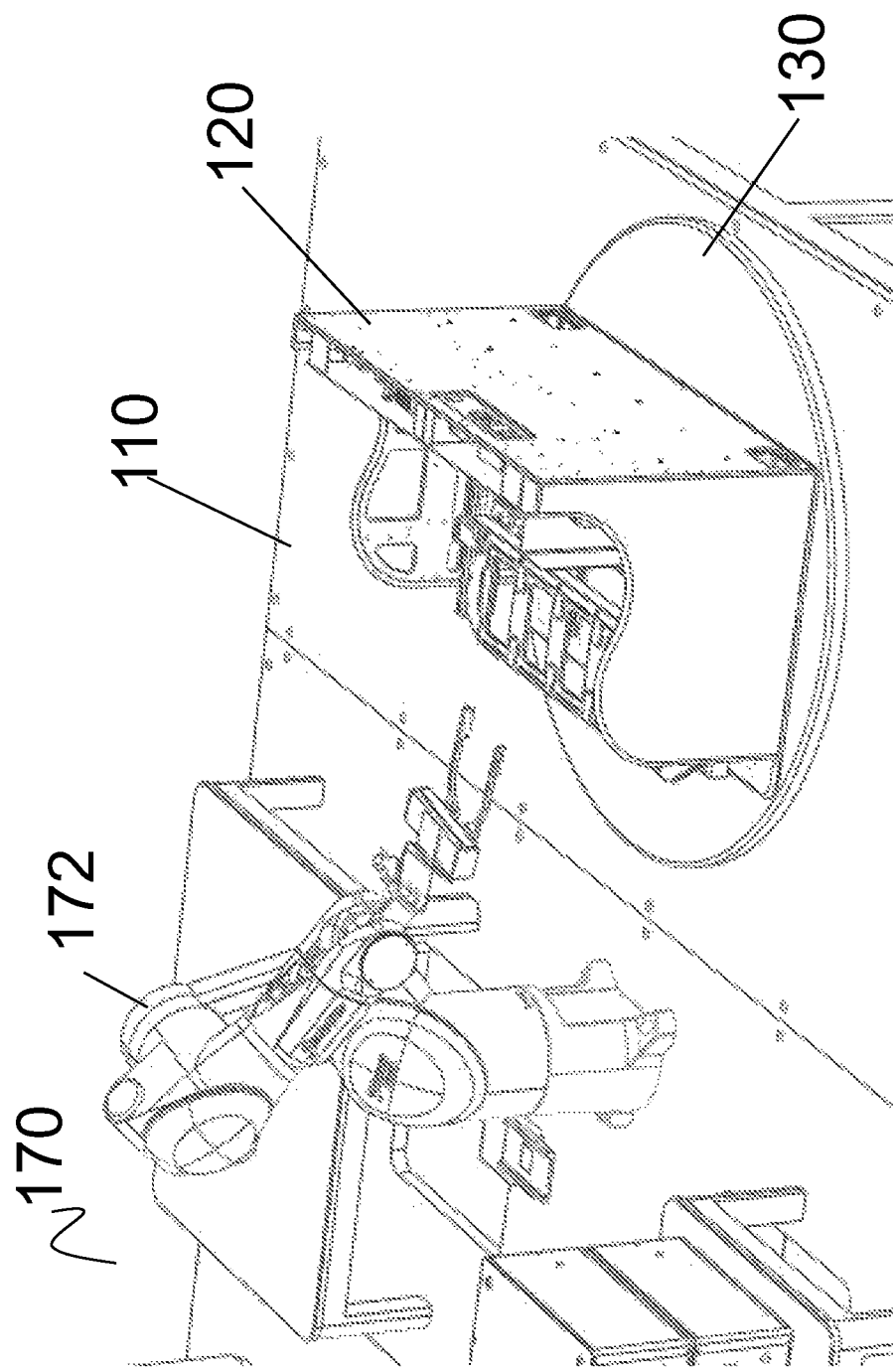
FIG. 8 shows a close up of a side perspective view of an instrument on a turntable in conjunction with an automated system.
Figure 9:
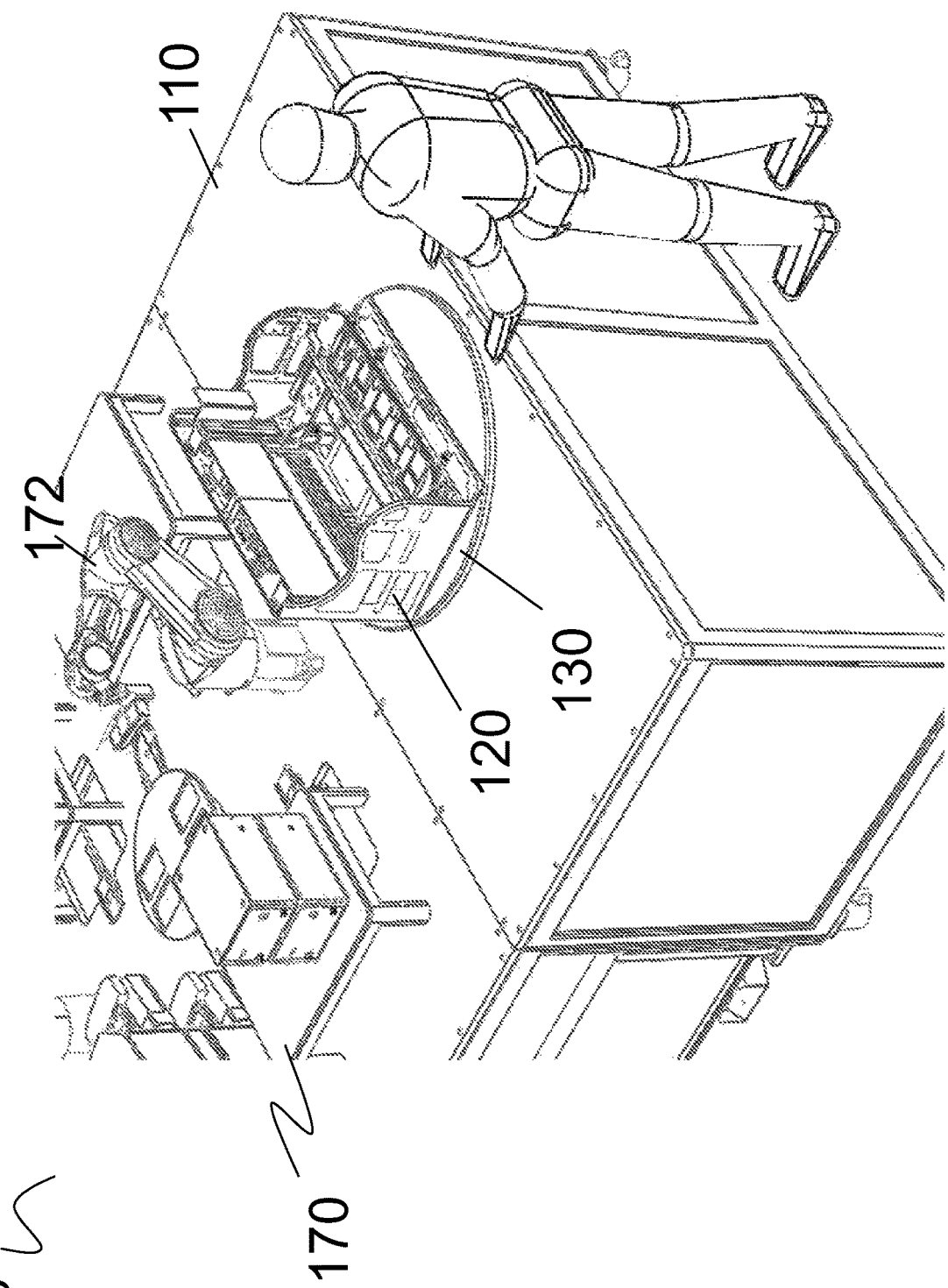
FIG. 9 shows a side perspective view of an instrument on a turntable in conjunction with an automated system turned toward a user.

FIGS. 7, 8, and 9 show system 100 with instrument 120 in various positions with respect to automated system 170 and, particularly, robotic arm 172.

The foregoing description of various aspects of the invention has been presented for the purpose of illustration and description. It is not intended to be exhaustive or to limit the invention to the precise form disclosed, and obviously, many modifications and variations are possible. Such variations and modifications that may be apparent to one skilled in the art are intended to be included within the scope of the present invention as defined by the accompanying claims.

What is claimed is:

1. A system comprising:
   a mobile cart;
   a surface on the mobile cart, the surface for holding an instrument, the instrument having an exterior user interface configured so as to define a predetermined singular primary facing bias that determines a predetermined singular front facing in a predetermined singular primary facing direction;
   a rotating element coupled to the surface to allow the surface to rotate, on the mobile cart between a first position and a second position, wherein the first position is arranged with respect to the instrument held on the surface such that the predetermined singular primary facing direction of the instrument is oriented towards an automated system and the second position is arranged with respect to the instrument held on the surface such that the predetermined singular primary facing direction of the instrument is oriented away from the automated system;
   a sensor to detect a position of the surface;
   a member for locking the surface in a holding position, wherein the member includes a spring loaded ball catch;
   and
   a device for sending a signal indicating the first position and the second position of the surface from the sensor to an automated system including a robotic arm for accessing the instrument, wherein the automated system is mounted separately from the mobile cart.

2. The system of claim 1, wherein the rotating element comprises at least one element selected from a group consisting of: a rotary turntable, a set of linear rails, a set of curved rails, a hinge, a set of eccentric rotary bearings, and a set of non-parallel linear rails.

3. The system of claim 1, wherein the sensor comprises at least one sensor selected from a group consisting of: a proximity sensor, an infrared beam sensor, a laser beam sensor, a rotary encoder, a linear encoder, and a linear differential transformer.

4. The system of claim 1, further comprising an actuator for turning the surface.

5. The system of claim 4, wherein the actuator includes at least one actuator selected from a group consisting of: an electric actuator or a pneumatic actuator.

6. The system of claim 4, wherein the actuator holds the surface in the holding position.

7. The system of claim 1, wherein the member for locking the surface is adapted to alternately lock the surface in a first position and a second position, wherein the instrument faces the automated system in the first position, and the instrument faces away from the automated system in the second position.

8. The system of claim 1, wherein the mobile cart moves independently of the automated system.

9. The system of claim 1, wherein the spring loaded ball catch includes a first part attached to the surface, and a second part housing a spring loaded catch ball.

10. The system of claim 1, further comprising a shock absorber coupled to the member that locks the surface.

11. The system of claim 10, wherein the shock absorber comprises at least one shock absorber selected from a group consisting of: a rubber pad, a foam pad, a pneumatic damper, a hydraulic damper, and a spring shock.

12. A method comprising:
    providing a system including:
      a mobile cart,
      a surface on the mobile cart, the surface for holding an instrument, the instrument having an exterior user interface configured so as to define a predetermined singular primary facing bias that determines a predetermined singular front facing in a predetermined singular primary facing direction,
      a rotating element coupled to the surface to allow the surface to rotate on the mobile cart between a first position and a second position, wherein the first position is arranged with respect to the instrument held on the surface such that the predetermined singular primary facing direction of the instrument is oriented towards an automated system and the second position is arranged with respect to the instrument held on the surface such that the predetermined singular primary facing direction of the instrument is oriented away from the automated system,
      a sensor to detect a position of the surface,
      a member for locking the surface in a holding position, wherein the member includes a spring loaded ball catch, and
      a device for sending a signal indicating the first position and the second position of the surface from the sensor to an automated system including a robotic arm for accessing the instrument, wherein the automated system is mounted separately from the mobile cart;
    placing the system in conjunction with the automated system, the automated system including the robotic arm; and
    sending the signal from the sensor to the automated system.

13. The method of claim 12, allowing the robotic arm access to an instrument on the system in response to the sensor detecting that the system is facing the automated system.

14. The method of claim 12, prohibiting the robotic arm access to an instrument on the system in response to the sensor detecting that the system is not facing the automated system.

15. The method of claim 12, wherein the mobile cart moves independently of the automated system.

16. The method of claim 12, wherein the spring loaded ball catch includes a first part attached to the surface, and a second part housing a spring loaded catch ball.

17. The Method of claim 12, further comprising locking the surface with a shock absorber coupled to the member.

* * * * *